(12) United States Patent
Nelson

(10) Patent No.: US 6,868,344 B1
(45) Date of Patent: Mar. 15, 2005

(54) CONTROLLED SUBSTANCE ANALYSIS, WASTAGE DISPOSAL AND DOCUMENTATION SYSTEM, APPARATUS AND METHOD

(75) Inventor: David Austin Nelson, Austin, TX (US)

(73) Assignee: Vigilant Devices, LLC, Austin, TX (US)

( * ) Notice: Subject to any disclaimer, the term of this patent is extended or adjusted under 35 U.S.C. 154(b) by 0 days.

(21) Appl. No.: 10/175,339

(22) Filed: Jun. 19, 2002

Related U.S. Application Data
(60) Provisional application No. 60/300,122, filed on Jun. 22, 2001.

(51) Int. Cl.[7] .............................................. G01N 21/65
(52) U.S. Cl. ........................................................ 702/31
(58) Field of Search ......................... 702/31, 19; 435/6, 435/7, 7.92; 436/523, 172, 518, 47, 86; 427/2, 421, 7; 428/195, 82; 422/82, 98; 382/128; 424/486; 604/318

(56) References Cited

U.S. PATENT DOCUMENTS

| | | | |
|---|---|---|---|
| 4,785,969 A | | 11/1988 | McLaughlin |
| 5,014,875 A | | 5/1991 | McLaughlin et al. |
| 5,272,094 A | * | 12/1993 | Barker et al. ................ 436/518 |
| 5,284,772 A | * | 2/1994 | Oxley .......................... 436/47 |
| 5,431,299 A | | 7/1995 | Brewer et al. |
| 5,713,485 A | | 2/1998 | Liff et al. |
| 5,745,366 A | | 4/1998 | Higham et al. |
| 5,797,515 A | | 8/1998 | Liff et al. |
| 5,805,456 A | | 9/1998 | Higham et al. |
| 5,842,976 A | | 12/1998 | Williamson |
| 5,898,503 A | | 4/1999 | Keller et al. |
| 5,905,653 A | | 5/1999 | Higham et al. |
| 5,912,456 A | | 6/1999 | Melendez et al. |
| 5,927,540 A | | 7/1999 | Godlewski |
| 5,946,083 A | | 8/1999 | Melendez et al. |
| 6,003,006 A | | 12/1999 | Colella et al. |
| 6,011,999 A | | 1/2000 | Holmes |
| 6,021,392 A | | 2/2000 | Lester et al. |
| 6,040,191 A | * | 3/2000 | Grow .......................... 436/172 |
| 6,045,756 A | | 4/2000 | Carr et al. |
| 6,068,156 A | | 5/2000 | Liff et al. |
| 6,097,479 A | | 8/2000 | Melendez et al. |
| 6,111,248 A | | 8/2000 | Melendez et al. |
| 6,111,652 A | | 8/2000 | Melendez et al. |
| 6,116,461 A | | 9/2000 | Broadfield et al. |
| 6,151,536 A | | 11/2000 | Arnold et al. |
| 6,183,696 B1 | | 2/2001 | Elkind et al. |
| 6,191,847 B1 | | 2/2001 | Melendez et al. |
| 6,326,210 B1 | | 12/2001 | Carr et al. |
| 6,326,612 B1 | | 12/2001 | Elkind et al. |
| 6,374,845 B1 | | 4/2002 | Melendez et al. |
| 6,488,669 B1 | * | 12/2002 | Sagona et al. ............... 604/318 |
| 6,558,956 B1 | * | 5/2003 | Carron et al. ................. 436/86 |
| 2004/0029117 A1 | * | 2/2004 | Olek et al. ...................... 435/6 |

OTHER PUBLICATIONS

"Refractive Index Sensing with Surface Plasmon Resonance, "©Texas Instruments, Inc. 1995–2002, pp. 1–3.

(List continued on next page.)

*Primary Examiner*—John Barlow
*Assistant Examiner*—Tung Lau
(74) *Attorney, Agent, or Firm*—Charles D. Huston; Daffer McDaniel, L.L.P.

(57) ABSTRACT

A method, system, and apparatus for the collection, analysis, and disposal of controlled substances are described. A collector receives an excess of controlled substance and stores the controlled substance so that unauthorized access is minimized. An analysis determines the chemical composition and concentration. The results of the analysis are reviewed and reconciled against information in an overseeing authority information system or against information provided by the depositor of the controlled substance or both. The controlled substance is disposed of once it has been confirmed that the substance deposited in the collector is the same substance claimed to be deposited and the same substance issued by the pharmacy or other qualified authorities.

21 Claims, 7 Drawing Sheets

OTHER PUBLICATIONS

"Involving anesthesiology in drug control," Am. J. Health Syst. Pharm., vol. 54, Jun. 1997, pp. 1392–1393.

McClary et al., "A Guide to Prescribing, Administering, and Dispensing Controlled Substances in Missouri," Missouri Medicine, vol. 96, No. 2, Feb. 1999, pp. 47–54.

Mallby et al., "Simple narcotic kits for controlled–substance dispensing and accountability," Can. J. Anaesth., vol. 41, No. 4, 1994, pp. 301–305.

Ashton et al., "Investigating Narcotic Diversion," Nursing Management, Mar. 1994, pp. 35–37.

Schmidt et al., "A Reliable Accounting System for Controlled Substances in the Operating Room," Anesthesiology, vol. 78, No. 1, Jan. 1993, pp. 184–190.

Hazebrook et al., "Computer system for determining trends in controlled–substance discrepancies," AJHP, vol. 48, Jun. 1991, pp. 1262–1264.

"Computerized system for controlled–substances distribution," Am. J. Health Syst. Pharm., vol. 54, Mar. 1997, pp. 630, 636.

"Rules Concerning Waste of Narcotics," Texas State Board of Pharmacy, Aug. 2000, pp. 211–212.

* cited by examiner

CONTROLLED SUBSTANCE ANALYSIS, WASTAGE DISPOSAL AND DOCUMENTATION SYSTEM, APPARATUS AND METHOD

This application claims the benefit of U.S. Provisional Application No. 60/300,122, filed on Jun. 22, 2001, entitled "Controlled Substance Analysis, Wastage Disposal And Documentation System, Apparatus, and Method."

BACKGROUND OF THE INVENTION

1. Field of the Invention

The present invention relates generally to the disposal of controlled substances such as medication. Specifically, this invention relates to a method, system, and apparatus for the collection of excess controlled substances (wastage), analysis of the wastage, and documentation of the wastage. Further, this invention relates to a method for collecting, analyzing, and documenting the wastage, as well as reconciling the documentation.

2. Description of Related Art

A controlled substance is a drug or drug product that comes under the jurisdiction of the federal Controlled Substances Act of 1970 and is distributed and used in accordance with the Comprehensive Drug Abuse Prevention and Control Act of 1971. A narcotic, depressant, stimulant, hallucinogenic or anabolic steroid drug that is covered is by the Controlled Substances Act (CSA) is obtained in a variety of ways by licensed facilities, pharmacies, or caregivers:

The drug is dispensed by the manufacturer or pharmaceutical supplier directly to the facility (i.e. hospital, laboratory, or patient care facility) or pharmacy.

A pharmacy directly dispenses the drug in a unit dose or as part of a drug pack, which may include varying amounts of controlled drugs.

A pharmacy may dispense these drugs through an automated drug dispensing system such as systems manufactured by Omnicell® (Palo Alto, Calif.) or Pyxis® (San Diego, Calif.). U.S. Pat. Nos. 5,797,515, 5,713, 485, 6,068,156, 6,011,999, 5,927,540, 5,905,653, 5,805,456, 5,745,366, 6,151,536, 5,431,299, 6,116, 461, 6,021,392, 6,003,006, 5,842,976, 5,014,875, and 4,785,969 disclose medication dispensing systems, methods, and devices.

Once the drug is obtained it is utilized in the prescribed manner either administered to a patient, utilized as part of an infusion, or utilized in a laboratory study. Frequently, there is an excess of the drug that must be disposed of in a controlled manner regulated by enforcement agencies such as the DEA, State Boards of Pharmacy, and state and local law enforcement agencies. Failure to adhere to their regulations can bring stiff penalties such as fines, imprisonment, and loss of license to handle and dispense controlled substances. Because of this, it is imperative for anyone involved in the use of controlled substances to strictly follow these regulations.

Policies of regulatory agencies and also patient care facilities dictate that any excess drug be disposed and rendered useless for human consumption. Also, the process of wasting these drugs must be a witnessed event. This requires the witness to visually observe the amount or volume of drug wasted and which drug is being wasted. The witness then confirms this by signature. The wastage witness signature is recorded either in handwritten form or on a computerized system (such as the case with Omnicell® or Pyxis® systems previously mentioned).

There are several serious shortcomings of the current disposal system and method:

Firstly, all injectable controlled substances are currently manufactured as clear liquids, meaning their appearance is the same as saline or even water. This creates the potential for easily substituting any other clear liquid for the controlled substance. The potential for theft of these drugs for self-medication or illicit sale remains high even with the strictest enforcement.

To document the wastage, the person wasting the controlled substance must find another person to witness the waste process and verify the process by way of a signature. In most facilities, this requires the signature of a person with an advanced clinical degree such as a Registered Nurse or an authorized clinician. During busy times this process may be delayed or forgotten.

The disposal process ("wasting") is also imperfect. Typically the controlled substance is disposed by injection into a sink, expelled onto the floor, or dropped into a needle disposal container. In the case of partially used vials of controlled substances, these are sometimes deposited intact into needle disposal containers and could potentially be retrieved for unauthorized or illicit use.

Once the controlled substance is wasted, the process must be documented. Documentation consists of recording information such as the patient's name, the name of the controlled substance and its concentration, and the quantity (e.g., volume) that is wasted. Frequently, the records are handwritten and therefore prone to the pitfalls of poor handwriting and illegibility during review. Other times, the records are generated through computerized dispensing system units such as Omnicell® or Pyxisg. These systems require both the person wasting the substance and the witness to log on and complete several screen commands to complete the process.

Once the documentation is complete, the record of the administration (i.e., the patient's record) must match that of the wastage process. This is a labor-intensive task that requires a pharmacy's staff to spend hours reviewing records and reconciling discrepancies that arise during reviews.

All steps in the current method are time consuming and laborious with potential for fraud. In addition, there is not a routine provision for verifying the actual composition and concentration of the wasted substance and no efficient means for disseminating the information surrounding the process. It is therefore desirable to have a method for accurately monitoring and documenting the disposal of controlled substances. Further, it is desirable to have an automated system and apparatus for collecting excess and unwanted controlled substances, rendering the controlled substances unusable for human consumption, documenting information about the collection and disposal of the controlled substances, and reconciling the information with other information systems.

SUMMARY OF THE INVENTION

In one broad respect, the present invention is directed to a method for disposing of controlled substances comprising the steps of: collecting a controlled substance from a depositor of said controlled substance; analyzing said controlled substance to verify at least a portion of said information; recording information about the chemical composition and concentration and amount of said controlled substance; and disposing of said controlled substance. In one narrow respect, the method further comprises the step of receiving information about the controlled substance from a depositor of the controlled substance, wherein the information received comprises chemical composition, concentration or amount or any combination thereof. In one narrow respect, the disposal step further comprises the step of rendering the controlled substance into a form unusable for human consumption. In another narrow respect, the step of collecting the substance comprises securing the controlled substance to prevent access by unauthorized persons. In another narrow respect, the step of obtaining information about said controlled substance comprises retrieving information from an automated injection system. In another narrow respect, the step of obtaining information about said controlled substance comprises the depositor entering information about said controlled substance including composition and amount. In another narrow respect, the step of analyzing said controlled substance comprises identifying the chemical composition, concentration, and volume of said controlled substance. In another narrow respect, the method for disposing of controlled substances further comprises: documenting information about said controlled substance; reviewing the analysis of said controlled substance; and reconciling the to documentation of said controlled substance against information stored in an overseeing authority information system. In a narrower respect, the step of reviewing the analysis comprises verifying said chemical composition, concentration, and volume of said controlled substance collected is identical to information provided by the depositor of said controlled substance. In another narrower respect, the step of reconciling the documentation includes comparing said information obtained from information systems with results discovered during said analysis and with information provided by the depositor of said controlled substance. In another narrower respect, said information stored in said overseeing authority information system is a Medication Administration Report. In another narrower respect, the step of reconciling said documentation is automatic upon receiving information from said analyzer, obtaining information about said controlled substance from said depositor, and receiving information from, said overseeing authority information system.

In another broad respect, the present invention is directed to a system for disposing of controlled substances, comprising: a collector for receiving and storing excess controlled substances; an analyzer for determining the composition of a controlled substance; and an information recorder for obtaining, storing, and transferring information related to the disposal of a controlled substance. In one narrow respect, the system for disposing of controlled substances further comprises overseeing authority information systems. In another narrow respect, the system further comprises a disposer operable to render a controlled substance into a form unusable for human consumption. In another narrow respect, the collector for receiving and storing excess controlled substances is operable to prevent diversion. In another narrow respect, information recorded by said information recorder is automatically reconciled against information recorded in said overseeing authority information systems. In another narrow respect, information recorded by said information recorder is obtained from an automated injection system. In another narrower respect, said information is encrypted during data exchange between said overseeing authority information system and said information recorder. In another narrower respect, said transfer of information from said recorder to said overseeing authority information system includes the step of authenticating the identity of said recorder by said overseeing authority information system.

In another broad respect, the present invention is directed to a device for use with a collector in the collection and disposal of excess controlled substances, comprising: an analyzer for determining the chemical composition of a deposited controlled substance; a recorder for documenting the reception and analysis of said deposited controlled substance, said recorder capable of storing all information in an electronic format; and a disposer for rendering the controlled substance unusable for human consumption. In another narrow respect, the analyzer is operable to identify the chemical composition of controlled substance, the concentration of controlled substance, and the quantity. In another narrow respect, the device is further configured to extract said controlled substance from an aerosol applicator, a vial, and in solid form.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

It is to be noted, however, that the appended drawings illustrate only exemplary embodiments of the invention and are therefore not to be considered limiting of its scope, for the invention may admit to other equally effective embodiments.

DESCRIPTION OF ILLUSTRATIVE EMBODIMENTS

The following examples are included to demonstrate embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 1:
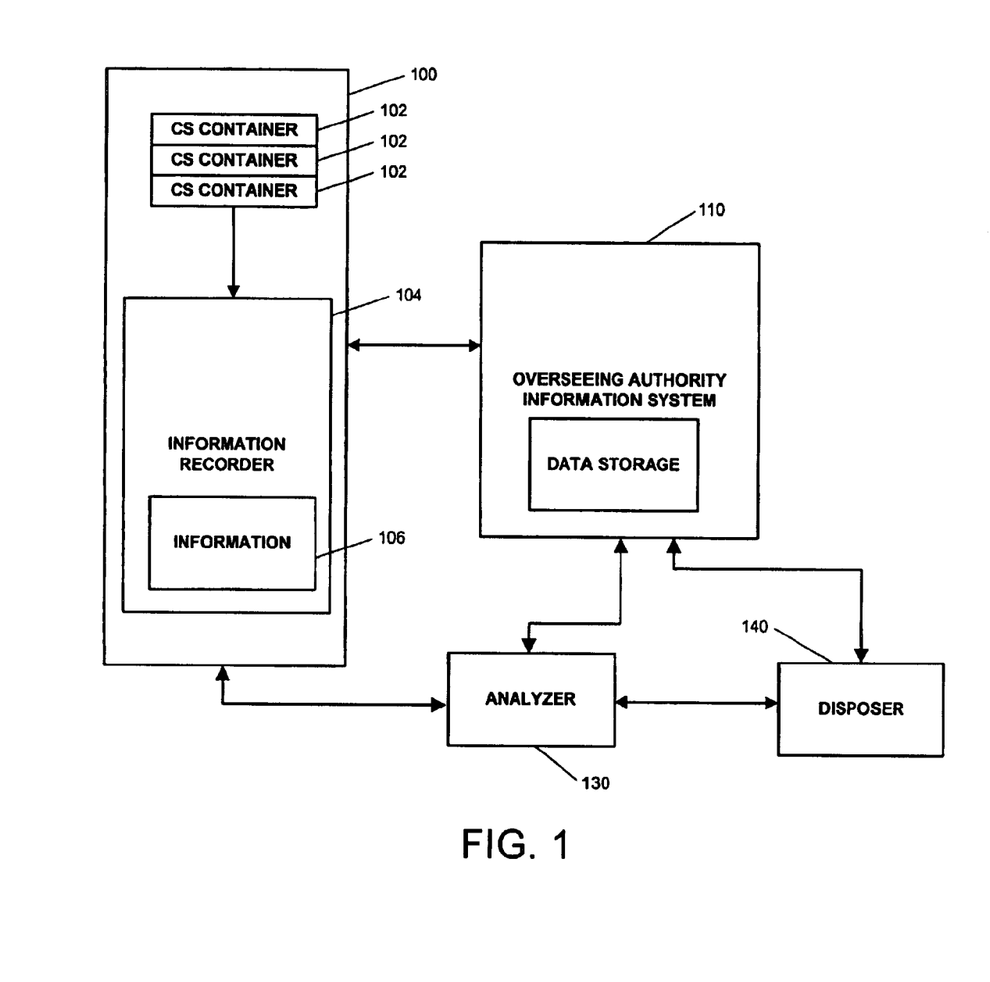
FIG. 1 is a high-level block diagram of a controlled substance disposal system in accordance with the present invention.

Referring to FIG. 1, a system in accordance with the present invention comprises a collector 100, an information recorder 104, an overseeing authority information system 110, an analyzer 130, and a disposer 140.

The depositor of a controlled substance deposits the controlled substance into the collector 100. The depositor provides information, which includes for example, depositor identification, patient information, and information about the controlled substance deposited in the collector 100, such as concentration, composition, and the amount. The collector 100 stores the information for each deposited controlled substance.

At some point in time, an authorized person commands the device to analyze the controlled substances deposited in the collector 100 with an analyzer 130. In some embodiments, the collector is integrated with the analyzer 130. In other -, the collector 100 or collectors 100 are located at various stations and must be collected and brought to the analyzer 130.

The analyzer 130 is used to determine the composition and concentration of the controlled substance deposited in the collector 100. Ideally, the analyzer 130 is capable of determining the composition and concentration without destroying the deposited substance, so that follow-up testing and verification of a sample is possible. In alternative embodiments, the analyzer 130 is capable of disposing of a controlled substance once the composition and concentration and amount are determined. In other embodiments, the analyzer 130 may be integrated with the disposer 140.

Multiple techniques are available for the analyzer 130. The analyzer 130 can analyze the controlled substance using for example ion mobility spectroscopy, visible or infra-red optical absorption spectroscopy, Raman scattering spectroscopy, fluorescence spectroscopy, gas chromatography, liquid chromatography, gas-liquid chromatography, mass spectrometry, capillary electrophoresis, surface plasmon resonance, optical biosensor array, semiconductor biosensor array, or by any spectrophotometric or spectrometric technique, or by a combination of techniques.

Five principal issues determine the choice of the analytical technique or combination of techniques that are needed for successful implementation of the analyzer 130:

Many different classes of substances must be identified, but at the same time the analyzer 130 must be capable of distinguishing between closely related substances, The analysis must be quantitative, and the analyzer 130 must be sufficiently accurate to detect dilution of wastage, to prevent diversion of a fraction of wastage followed by make-up with another clear liquid to compensate for the diverted volume:

If the analyzer 130 uses disposable elements to identify and quantify controlled substances, the calibration of the disposable elements must be certified and traceable to standards acceptable to regulatory agencies;

The results of the analysis must be available within an acceptably short period of time. Otherwise practitioners would be delayed in returning to their clinical duties while awaiting the analytical results;

The analyzer 130 must be sufficiently sensitive to identify and quantify concentration over a wide dynamic range. To illustrate this point, the narcotic fentanyl (fentanyl citrate) is supplied at a concentration of 0.05 mg/mL (50 parts per million) because of its high potency, and in some circumstances may be further diluted to only 0.02 mg/mL before administration. In contrast the narcotic meperidine (meperidine hydrochloride) may be supplied and administered at a concentration of up to 100 mg/mL (100,000 parts per million) since it is of lower potency.

Optical signals obtained from small quantities of dilute aqueous solutions are often weak, and may be below the lower sensitivity limits for Infrared spectroscopy, UV fluorescence spectroscopy, Raman spectroscopy, and similar photometric analytical techniques. Special apparatus and methods have been developed to address the optical signal strength issue, based on increasing the optical path length of the excitation beam within the analyte as it is caused to flow through a capillary tube. Examples of such signal enhancements are described by Gilby et al., 1993, U.S. Pat. No. 5,184,192 for photometric techniques in general; Liu, 1995, U.S. Pat. No. 5,444,807 for absorption and fluorescence measurements; Che et al. 1997, U.S. Pat. No. 5,604,587 for Raman scattering spectrometry; Niemela et al., "A capillary waveguide for use in Raman measurements of aqueous solutions", Report of Research Activities in Optoelectronics and Electronics Manufacturing, publication of VTT Electronics, Oulu, Finland (1999), also for Raman spectroscopy. In a variation of the use of the capillary as described in these references, Fein et al., 2000, U.S. Pat. No. 6,016,372, describe the use of the optical waveguide capillary such that it also functions as a permeable membrane to allow passage of a gaseous or liquid reagent to the interior of the capillary where its reaction with the analyte may be detected, or the reaction products may be detected.

A number of the possible techniques have been developed to the point where they can detect parts-per-billion of target substances. These techniques are typically applied to the detection of contraband substances such as narcotics or explosives in the baggage or on the persons of air travelers or building entrants. However, this extreme sensitivity is frequently associated with highly specific target substances, and the techniques often do not provide adequate quantification for a broad range of substances, as required for this application.

The following techniques are available, but for the purpose of this invention, any analysis technique that produces a precise analysis of the composition, concentration, and amount of a controlled substance may be used.

Day et al., 1996, U.S. Pat. No. 5,508,525 disclose the use of infrared absorption spectroscopy.

Kunz, 2001, U.S. Pat. No. 6,239,428 describes ion mobility spectrometers and methods.

Shiramizu, 2001, U.S. Pat. No. 6,248,997 describes the use of gas chromatography. 00321 Yamada et al., 2000, U.S. Pat. No. 6,058,764 describes a use of liquid chromatography.

Oberhauser, 2001, U.S. Pat. No. 6,190,550 describes a use of high performance liquid chromatography.

Truett, 1998, U.S. Pat. No. 5,728,301 describes a use of thin layer chromatography.

Wenzhi, 1996, U.S. Pat. No. 5,589,069 describes a method of ion chromatography.

Muller, 1997, U.S. Pat. No. 5,667,692 describes a use of gel permeation chromatography.

Gao, 2000, U.S. Pat. No. 6,156,196 describes the use of column chromatography.

Partition chromatography uses liquids adsorbed onto the solids and serving as adsorbents.

Paper chromatography uses a strip of adsorbent or absorbent paper. A liquid sample flows along the paper, depositing components in specific locations.

Gas-liquid chromatography separates mixtures of substances that have been vaporized by heat. An inert gas forces the vaporized mixture along a narrow, coiled, tube packed with material. The components flow at different rates and are detected at the end of the tube. Gas-solid chromatography is a variation.

Hennig, 2001, U.S. Pat. No. 6,246,238 describes the use of nuclear magnetic resonance spectroscopy. Alfano et al., 2001, U.S. Pat. No. 6,248,997 describes the use of fluorescence excitation spectroscopy.

Mass spectroscopy identifies substances based on the mass spectrum of the fragmentation patterns of molecules. In mass spectroscopy, a substance is placed in a vacuum, vaporized, ionized, and given extra energy, which cause the individual molecules to fragment. These fragments are separated based on weight by electric and magnetic fields in a mass analyzer.

Capillary electrophoresis is a standard method for separating organic molecules, based on their differing mobility in a liquid or gel, under the influence of an applied electric field. After separation the components may be identified using UV fluorescence spectroscopy, and thus this combination of techniques is especially applicable to mixtures of substances.

In "Surface Plasma Oscillations and Their Applications," Physics of Thin Films, 1977, H. Rather describes the use of surface plasmon resonance for chemical analysis. Surface plasmon resonance is exhibited when photons are reflected from a dielectric interface which has been coated with a thin layer of metal, typically gold. Under specific conditions of illumination, total internal reflection at the dielectric interface is altered by a material adsorbed on the thin metal film, creating a sharp shadow at an angle specific to the chemical composition of the adsorbed film. The change in internal reflection is caused by resonance energy transfer between the evanescent wave and surface plasmons within the adsorbed layer material. There is a relationship between the surface plasmon resonance signal and the mass concentration of material at the reflecting interface, though this is not necessarily linear, in which case the technique may be used quantitatively only after instrument calibration. By sensitizing the interface with a ligand specific to the analyte, and dissociation reactions between analyte and ligand may be monitored, and a sensor may be constructed which is highly selective and sensitive to specific analytes. The Spreeta™ Analytical Sensor produced by Texas Instruments is one example of a liquid analytical sensor for determining the chemical composition of a fluid based on surface plasmon resonance. U.S. Pat. Nos. 6,374,845, 6,326,612, 6,326,210, 6,191,847, 6,183,696, 6,111,652, 6,111,248, 6,097,479, 6,045,756, 5,946,083, 5,912,456, and 5,898,503 (all assigned to Texas Instruments) describe various sensors utilizing surface plasmon resonance technology.

McAndrew et al., 2000, U.S. Pat. No. 6,154,284 describes the use of gas absorption spectroscopy.

Eastan et al., 1999, U.S. Pat. No. 5,880,832 describes a use of spectrophotometry.

Atomic emission and atomic absorption spectrophotometry analyze elements based on energy characteristics of electromagnetic radiation emitted by the sample. Using these techniques, the sample is heated to a high temperature and decomposed into atoms and ions that absorb or emit visible or ultraviolet electromagnetic radiation at energies characteristic of the elements involved.

Raman scattering detects the wavelength shift of photons which have; been absorbed and re-emitted after losing a fraction of the energy of the received (excitation) photons when that energy excites a molecular vibrational or rotational mode in the scattering medium. Since the modes available for this process depend on the molecular structure of the scattering material, the Ratnan spectrum is determined by the scattering material.

Biosensor arrays identify the presence of target molecules within analyte by detecting the binding of the targets to ligands. The ligands are chosen to be specific to each target of potential interest. The ligands form an array of microscopic sites, each site being coated with a single ligand. When such an array is brought into contact with analyte, the sites which exhibit binding are detected, and their location identifies which target or targets are present in the analyte. The binding process may be detected by various methods, generally either optical or electronic.

In the optical case, the analyte may be pre-treated with a fluorescence marker such as fluorescein, which attaches to the target molecules. After the binding, illumination of the array with a fluorescence-exciting beam of light creates fluorescence at the sites where binding has occurred, and this fluorescence is detected. Alternatively, the ligands may be formed into diffraction gratings, and the binding alters either the height or refractive index of the diffraction grating elements, thus altering the diffraction pattern which results when the gratings are illuminated with coherent light.

In the electronic case, the array sites are on the surface of a semiconductor chip which measures surface electrochemical potential at each site, and the binding is detected by an associated change in surface electrochemical potential.

Once the analyzer 130 has determined what substance was deposited into the collector 100, the records are reviewed and reconciled. During the review process, information stored in the collector 100 is compared with the results of the analysis performed by the analyzer 130. In an exemplary embodiment, a successful review would indicate the information about the substance deposited in the collector 100 is identical to the information provided by the depositor. An unsuccessful review would indicate information about the substance deposited in the collector 100 is not identical to information provided by the depositor. For example, review might indicate that the substance differed in concentration, composition, and/or amount from the information collected from the depositor. In the event of an unsuccessful review, the substance deposited in the collector 100 may optionally be retested or stored for further review at a later time or action, such as a disposal, or medication error. While in most cases 100% testing is anticipated, the frequency of analysis may be based on statistical parameters.

For acceptance by regulatory authorities as a substitute for the existing witness system, the analyzer 130 may desirably be enclosed within a tamper-resistant or tampere-vident enclosure. Such an enclosure prevents two types of fraudulent practice:

Diversion of controlled substances, for example by alteration of the wastage handling components within the device;

Manipulation of the calibration of the analyzer 130 such that quantities or concentrations less than nominal would generate acceptable values.

Securing the analyzer 130 against tampering may be accomplished by using an enclosure which is locked in any conventional way to provide tamper resistance. Alternatively the analyzer 130 may be opened freely, but only by breaking seals applied by regulatory agencies, thus providing evidence of tampering.

After the analysis, the information about the amount of the controlled substance recorded is reconciled against information stored in an overseeing authority information system (OAIS) 110. Information (stored in the OAIS 110) about the amount of the controlled substance could include for example a patient's Medication Administration Report (MAR), an anesthesia record, or a pharmacy report of the quantity of the administered controlled substance. In an exemplary embodiment of the present invention, a successful reconciliation would indicate that information provided by the depositor is identical to information provided by the OAIS 110 and provided by the analyzer 130. An unsuccessful reconciliation would indicate the information provide by the depositor about the quantity of the controlled substance deposited in the collector 100 is not identical to the information stored in the OAIS 110 or provided by the analyzer 130. In the event of an unsuccessful reconciliation, the overseeing authority is notified so the discrepancy can be investigated.

During the disposal processes, the collector 100 and overseeing authority information system 110 are operatively coupled to enable the transfer of information. As used in this disclosure, "operatively coupled" means connected in such a way that data may be exchanged. It is understood that "operatively coupled" does not require a direct connection, a wired connection, or even a permanent connection. It is sufficient for purposes of the present invention that the connection(s) be established for the sole purpose of exchanging information. The connection may be across a network, the in Internet, an intranet, or dedicated lines.

The usefulness of the invention requires that data received by the OAIS 110 not be subject to fraudulent manipulation which would allow diversion of controlled substances. Two fraudulent schema are anticipated:

Valid data from an authorized analyzer 130 may be intercepted and altered during transfer to the OAIS 110;

Bogus analyzers may be inserted onto the network, to send data to the OAIS 110. For instance, a computer on the network may simulate an authorized analyzer 130 and send data packets as if they came from that analyzer 130, or even mimic an analyzer 130 which does not physically exist.

Both types of fraud are well known, and constitute security risks for which accepted counter-measures are commonly deployed:

Sensitive data to be transmitted over a network may be encrypted, so that it cannot be read or manipulated by parties other than the intended recipient, the OAIS 110 in this case;

To prevent bogus analyzers 130 being deployed, two steps must be taken: identification and authentication of both the analyzer 130 and the individual using it. The simplest implementation is a username and password combination, but this has weaknesses such that it may not be considered adequately secure. More elaborate systems use a trusted third party server which provides a short-term session digital encryption key which is used to generate an authenticator which can be verified by the intended recipient, the OAIS 110 in this case. Each data transmission is thus accompanied by a temporary digital signature which could only have been generated by an authorized analyzer 130 operated by an authorized practitioner. If the OAIS 110 is itself an acceptably secure server, it may act as the trusted third party in this case.

The security measures which are adopted must not be burdensome on practitioners, since the usefulness of the invention depends on improving the efficiency of the wastage process. In particular, keyboard operation and mouse manipulation should be minimized while meeting the need for practitioner identification and authentication. In this context the wastage system may usefully include a biometric individual identification and authentication method such as fingerprint or retinal scan, or the use of a secure individual physical token method such as a smart card.

Once a successful review and successful reconciliation are completed, the controlled substance is rendered unusable for human consumption by a disposer 140. Rendering the substance unusable may be accomplished by chemical, thermal, or mechanical processes. The overseeing authority information system 110 may, optionally be updated to indicate the results of the disposal of a controlled substance.

Referring to FIGS. 2A, 2B 3A and 3B, the collector 100 contains separate compartments 102 capable of receiving liquids injected from a syringe 20 and storing liquid substances in a secure manner, and an information recorder 104. For the purpose, of this disclosure, storing substances in a secure manner means preventing diversion, theft, and other intentional acts to retrieve the substances, as well as preventing spillage and losses due to accidents, for example inadvertently dropping the collector 100 on the floor. The collector 100 may be configured in such a manner as to allow a depositor to inject a controlled substance directly into a compartment 102. Alternatively, the collector 100 may be capable of allowing a depositor to deposit a controlled substance in different forms including a solid form such as a pill or tablet, in liquid form but still in the vial or syringe 20, or in aerosol form still in the container.

The information recorder 104 stores information about the deposited substance. In a preferred embodiment, the information is provided by the depositor of the substance. The depositor may provide information by using a keyboard 150, mouse, optical character recognition, barcode scanner, or any other technique that will provide accurate, legible information to the information recorder 104. In other embodiments, the information is acquired automatically from the secure substance container 102. Information may be provided by a combination of depositor information and secure substance container 102 information. For example, the controlled substance container 102 may be configured to automatically detect the quantity deposited in a container 102 and send that information to the information recorder 104. In other embodiments, the present invention is operatively coupled to an automated injection system. In these embodiments with an automated injection system, the information stored in the information recorder 104 may further be compared with information provided by the automated injection system.

The analyzer 130 may use any technique discussed above to precisely determine the chemical composition and concentration of the substance as well as the quantity. Once the analyzer 130 has determined the composition and concentration of the substance, the information is reviewed and reconciled against information stored in the overseeing authority information system 110. In some embodiments, the review and reconciliation processes are conducted automatically by the overseeing authority information system 110. In other embodiments, information from the overseeing authority information system 110 is transmitted to the analyzer 130 for comparison. A possible advantage for sending information about a controlled substance to the analyzer 130 is to aid in the selection of analysis techniques. For example, if the depositor has indicated the substance is a certain type of sedative and there is an analysis technique better suited for analyzing sedatives related to that substance, then information provided by the overseeing authority information system 110 may be helpful in providing a more accurate analysis.

The overseeing authority information system (OAIS) 110 is a centralized system for storing and processing information. Information stored in the OAIS 110 may include for example, a patient's Medication Administration Report (MAR), a pharmacy report of medications, an anesthesia record, records from an automated injection system, and other types of data.

Once a controlled substance has been analyzed and the records relating to its use are reviewed and reconciled, the substance is rendered unusable in a disposer 140. Rendering the substance unusable may include chemical, thermal, and mechanical techniques and processes. Additionally, information from the disposer 140 and analyzer 130 may be transmitted to the OAIS 110 and stored in data storage 112.

Figure 2A:
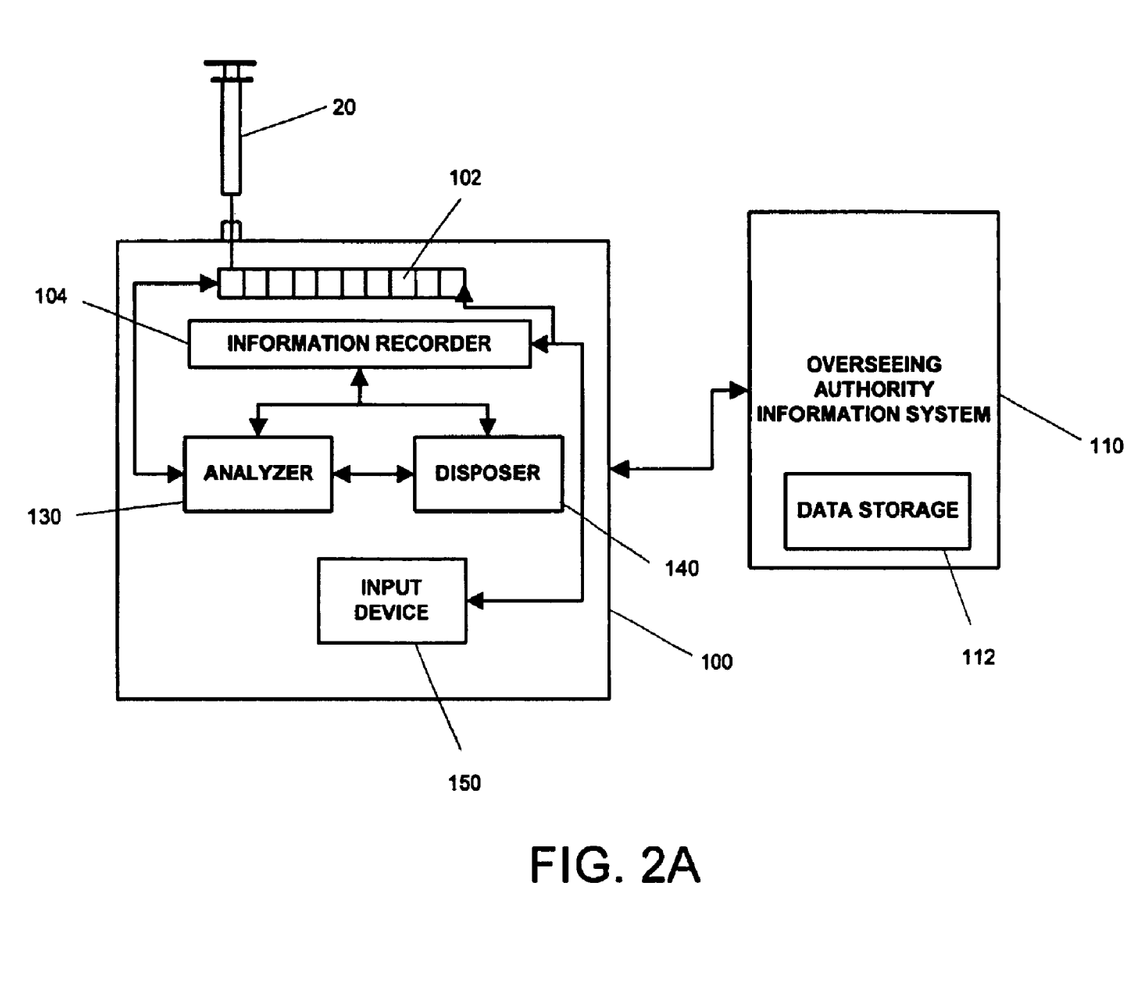
FIG. 2A is a block diagram of a controlled substance disposal system according to one embodiment of the disclosed invention.
Figure 2B:
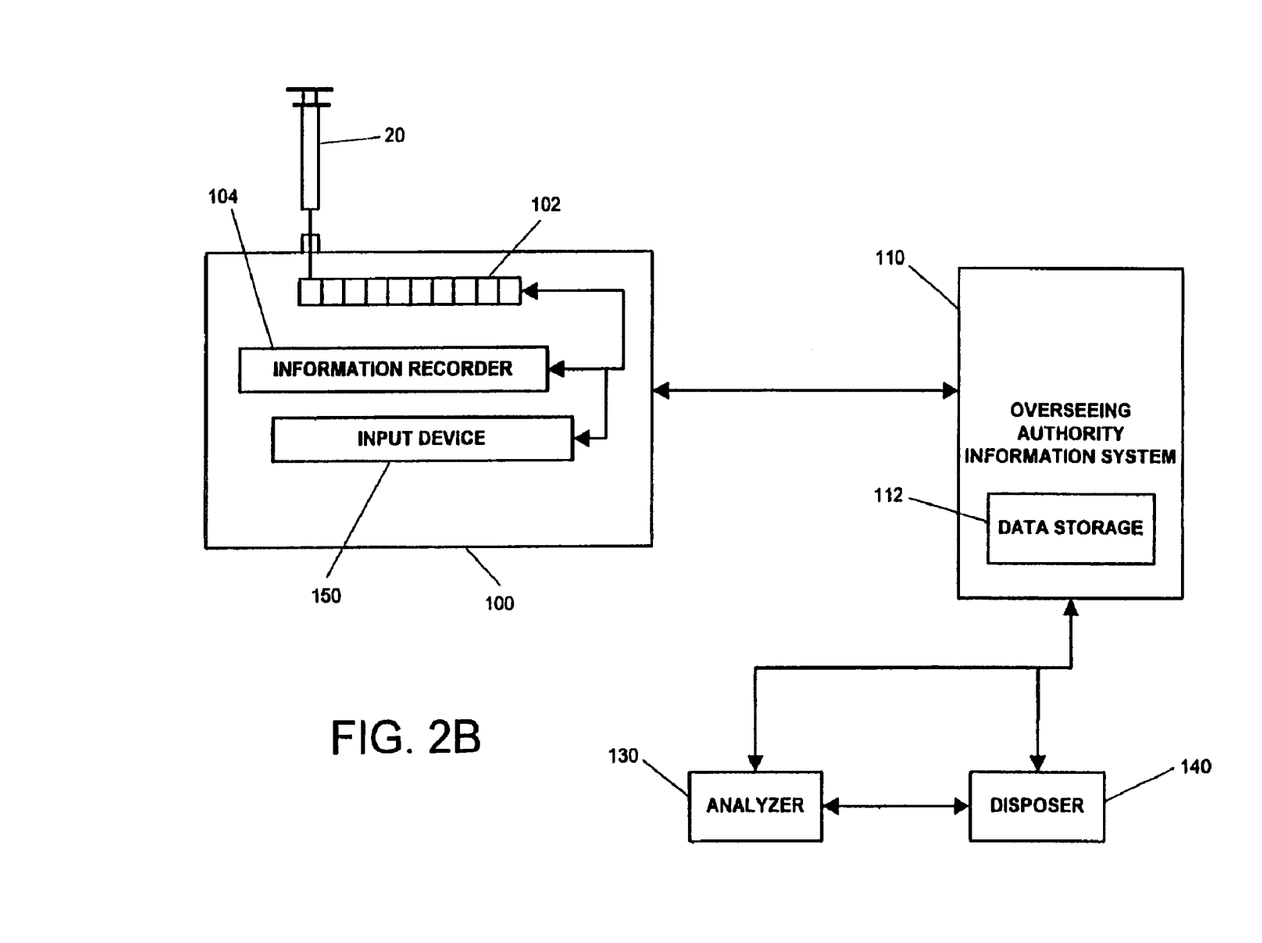
FIG. 2B is a block diagram of a controlled substance disposal system according to one embodiment of the disclosed invention.

FIG. 2A is one embodiment of the present invention in which the collector 100, analyzer 130, and disposer 140 are contained in the same structure. FIG. 2B is another embodiment in which the collector 100, analyzer 130, and disposer 140 are stand-alone devices. The embodiment shown in FIG. 2B may furter include multiple collectors 100, each collector 100 operatively coupled to the OAIS 110 and distributed throughout a facility. For example, each floor or department of a hospital might have a collector 100 for accepting multiple deposits of controlled substances. Each deposit is identified with information provided by the controlled substance depositor. Periodically or when nearing capacity, the collectors 100 of controlled substances are transferred to a central lab in the hospital for analysis.

Figure 3A:
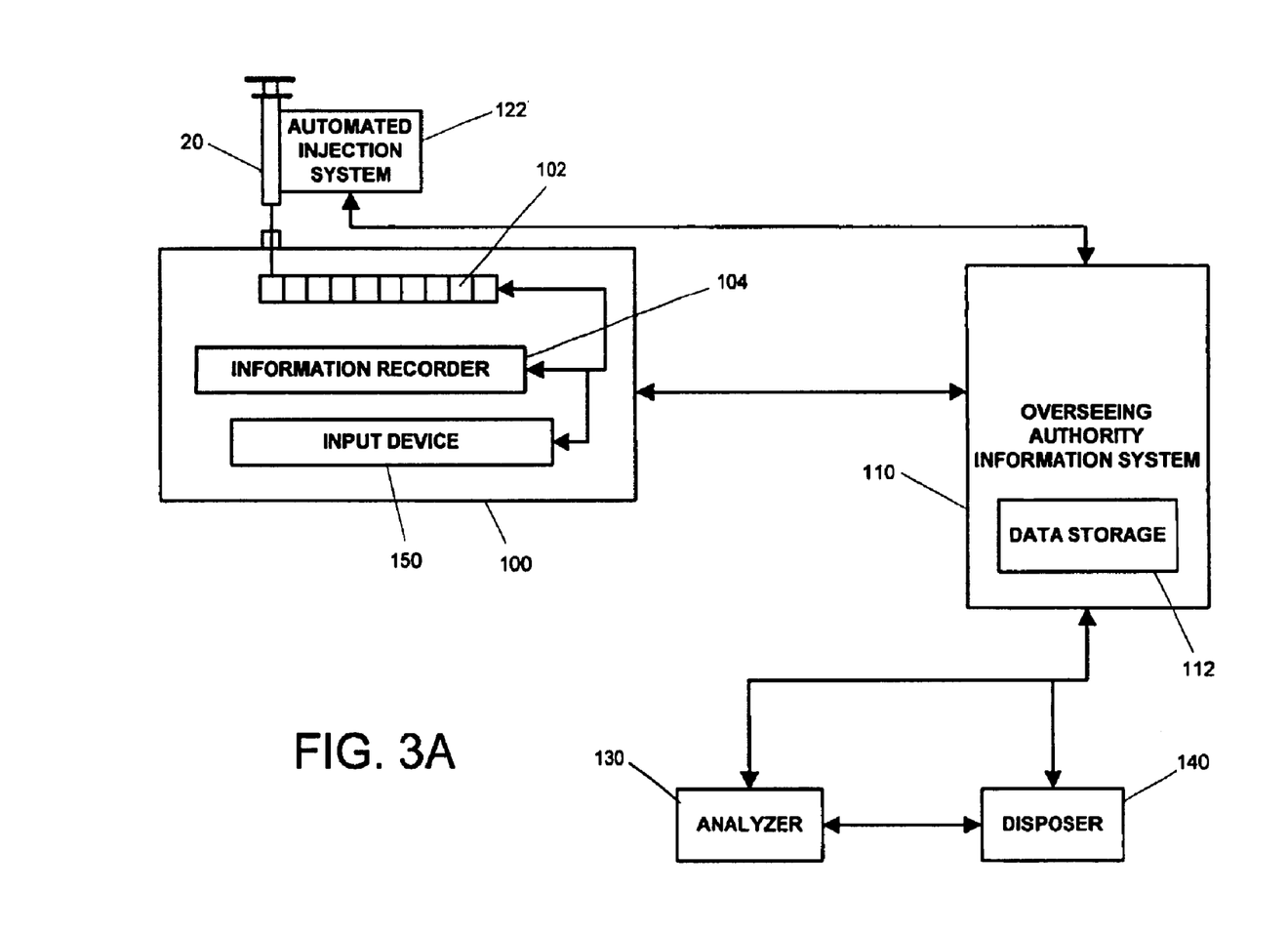
FIG. 3A is a block diagram of a controlled substance disposal system according to one embodiment of the disclosed invention.

FIG. 3A is another embodiment of the present invention, which includes an automated injection system 122. The automated injection system 122 may be operable to directly deposit excess medication into a collector 100 and further automatically inform the overseeing authority information system 110. In other embodiments, the present invention is operable to determine the chemical concentration and concentration of a controlled substance by using a technique that allows detection while the controlled substance is still in the syringe 20. For example, the Docuject™ system produced by Docusys™ (Mobile, AL) is an automated injection system that can inject a specific amount of a controlled substance from a syringe 20 in a syringe label cradle. Embodiments of the present invention may analyze the contents of the syringe 20 and compare this information with the bar code on the syringe label cradle. In such embodiments, the present invention may be able to analyze the controlled substance and dispose of the controlled substance without the need for receiving the controlled substance into the collector 100. In other embodiments, the present invention is adapted to receive a controlled substance from a syringe pump (not shown), for example, the syringe pump produced by Baxter (Deerfield, Ill.) under U.S. Pat. No. 5,971,722.

Figure 3B:
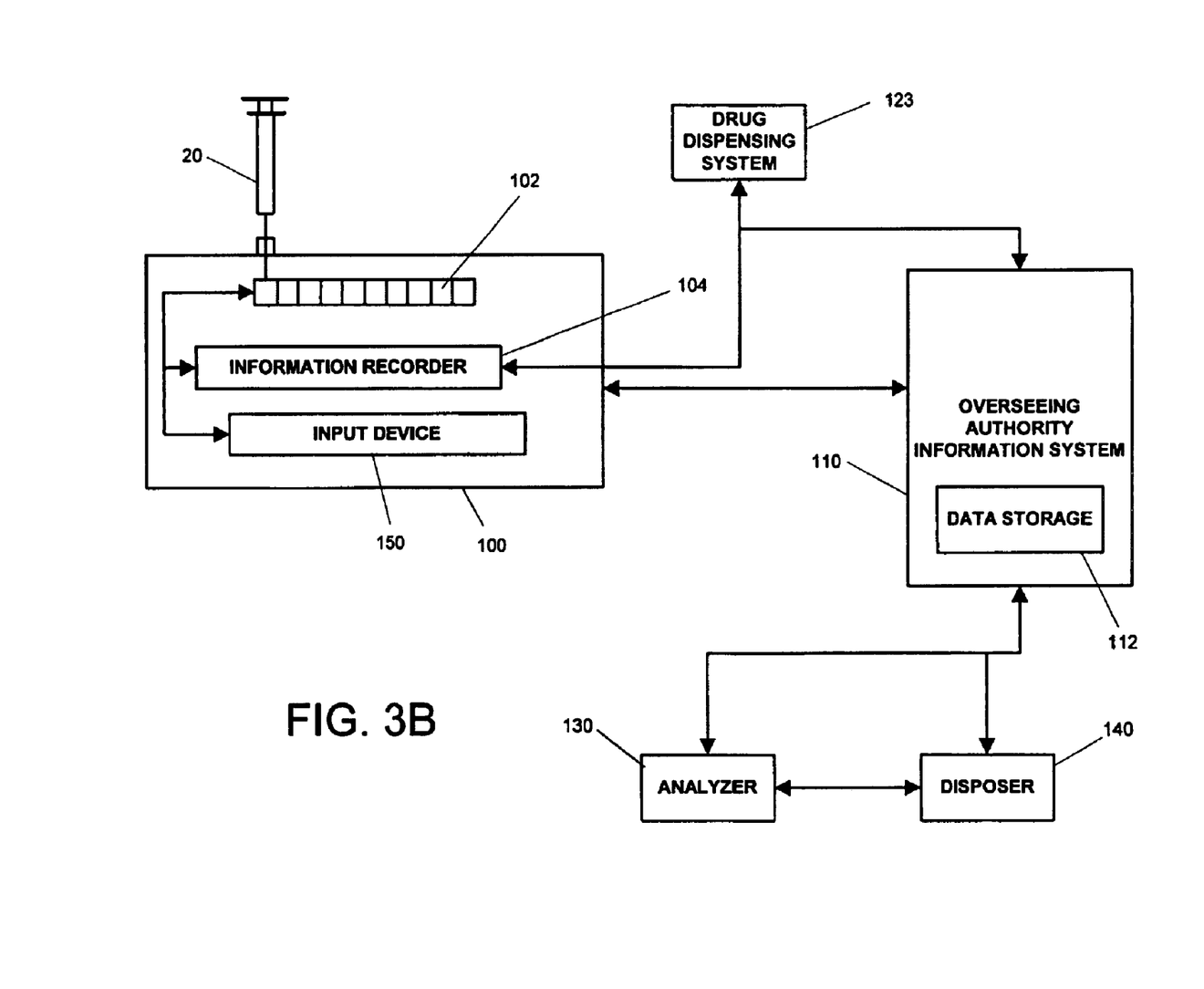
FIG. 3B is a block diagram of a controlled substance disposal system according to one embodiment of the present-invention.

FIG. 3B is another embodiment of the present invention, which includes an automated drug dispensing system 123 such as systems manufactured by Omnicell® (Palo Alto, Calif.) or Pyxis® (San Diego, Calif.). Information recorded by a drug dispensing system 123 is sent to the OAIS 110 and the collector 100.

Figure 4:
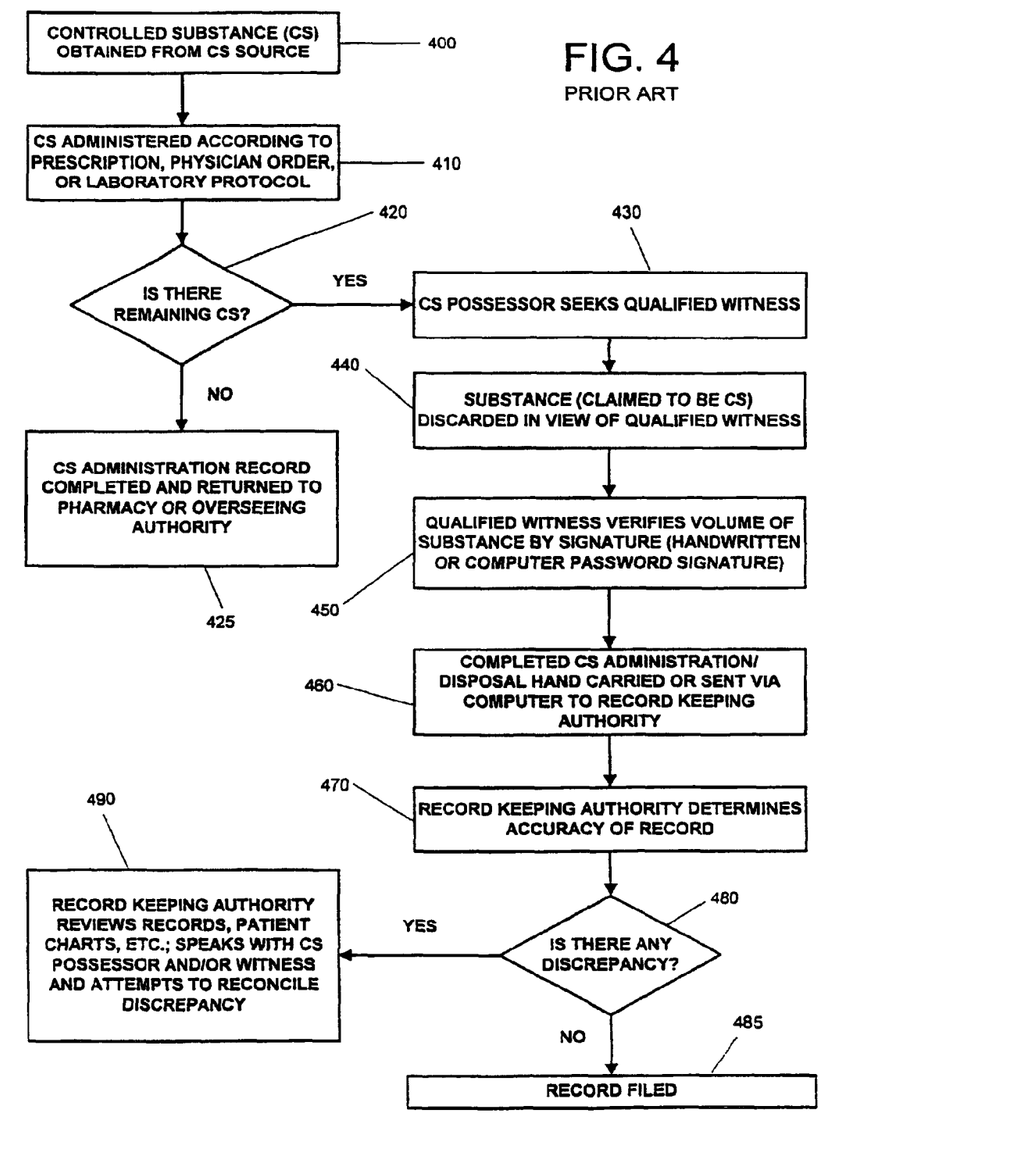
FIG. 4 is a flow chart of the prior art method for the disposal of controlled substances.

The flowchart in FIG. 4 illustrates the current processes involved for the disposal of controlled substances. In step 400, a controlled substance is obtained from the controlled substance source, for example a pharmacy. In step 410, the controlled substance possessor administers the controlled substance according to a prescription, physician order, or laboratory protocol.

In step 420, the possessor determines if there is excess controlled substance. If there is no excess of controlled substance, the possessor completes the required administration record and returns the record to the pharmacy or overseeing authority 425.

In step 430, the possessor has determined there is an excess of controlled substance and must dispose of the substance and therefore seeks a qualified witness.

In step 440, the possessor discards the substance while the witness observes. Typically, discarding a substance involves washing the liquid down the sink. As mentioned above, all injectable medications are currently clear, so the possibility exists for the possessor to substitute any clear liquid such as saline or water and the witness may not be able to notice a difference.

Once the substance has been discarded in full view of the witness 440, the witness verifies the volume of the substance by signature. The signature may be a handwritten signature or an electronic signature or password 450. After the witness verifies the disposal, the completed controlled substance administration record is completed and carried or sent via computer to the record keeping authority 460. Again, handwritten entries on the administration form contribute to errors that must be corrected.

In step 470, the record keeping authority then determines the accuracy of the record. If there is no discrepancy 480, the record is filed 485. If there is a discrepancy, the record keeping authority reviews records, patient charts, etc., and speaks with the possessor and witness in an attempt to reconcile the discrepancy 490. Unfortunately, the record keeping authority frequently does not have an opportunity to review and reconcile the records immediately. Additionally, the records may have errors due to handwriting, the possessor completing several disposals at the same time, and the time lapsed between the administration of the controlled substance and the disposal of any excess.

Figure 5:
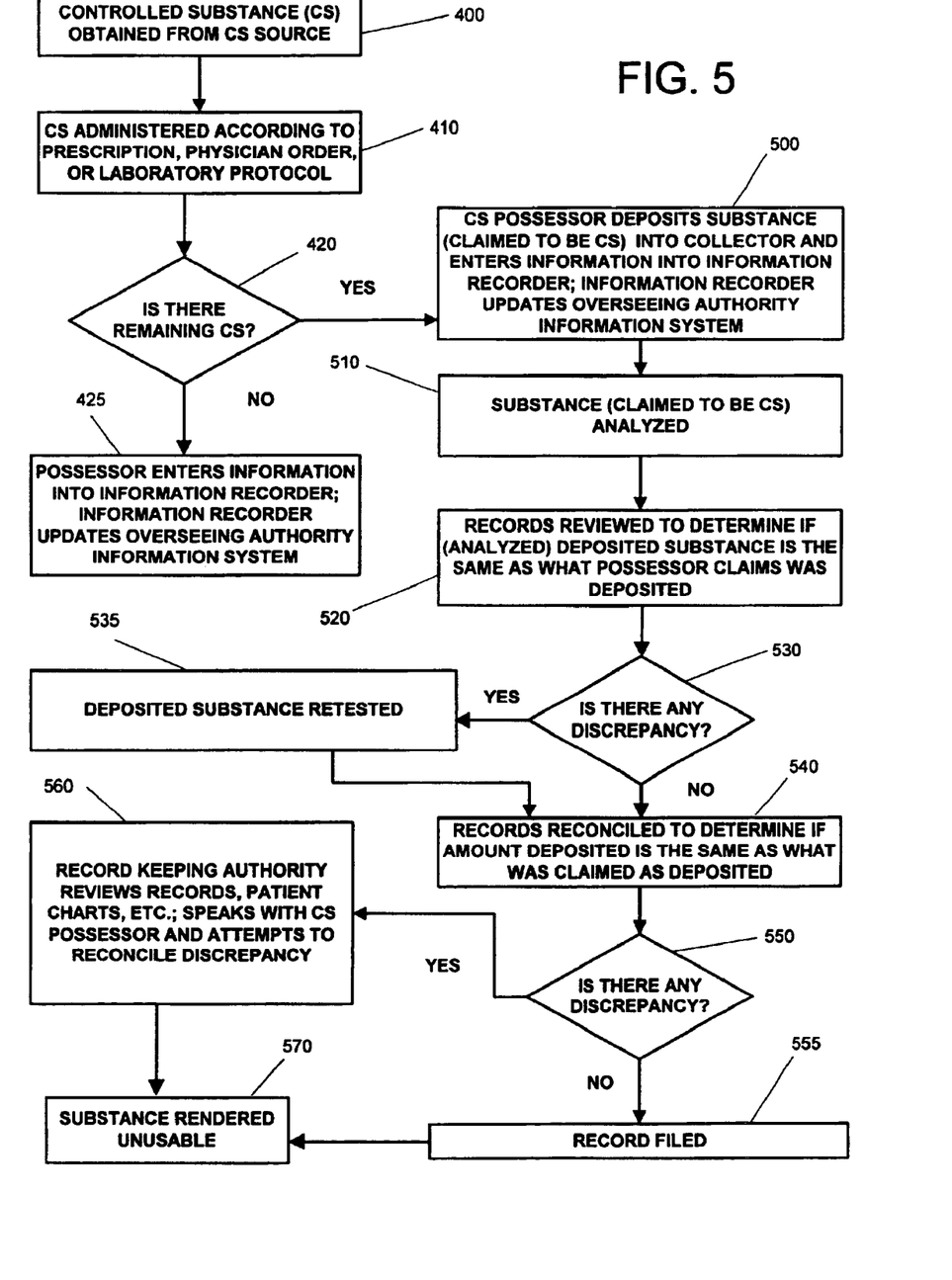
FIG. 5 is a flowchart of the disposal of a controlled substance according to one embodiment of the invention.

Referring to FIG. 5, the present invention describes a method for disposing of controlled substances in accordance with the present invention (where like steps are numbered similarly to FIG. 4). In step 400, a controlled substance is obtained from a controlled substance source, and in step 410, the controlled substance is administered according to a prescription, physician order, or laboratory protocol. In step 420, the possessor determines if there is any controlled substance remaining if not, then in step 425 the possessor enters the information about the transaction into the information recorder 104 and the information recorder 104 sends the information automatically to the overseeing authority information system 110. If there is controlled substance remaining, the possessor (now referred to as the depositor) deposits the substance into a collector 500 and provides information to the collector regarding the patient, depositor, and controlled substance.

In step 510, the substance is analyzed using any technique that accurately determines the composition, concentration and quantity of the substance.

In step 520, records are reviewed automatically by the device to determine if the analyzed deposited substance is the same substance that was claimed to be deposited by the depositor.

In step 535, if there is a discrepancy, the substance can be retested by the analyzer. Alternatively, the substance may be stored in a separate collector 100 or any other secured container for testing by another device or facility, such as an off-campus site.

If there is no discrepancy and the analyzer has determined the deposited substance is the same composition and concentration as the information provided by the depositor, the records are then reconciled to determine if the quantity or amount of the deposited substance was essentially the same as what was claimed by the depositor 540. If there is no discrepancy 550, the record is filed 555 and the substance is automatically rendered unusable for human consumption 570. If the information provided by the depositor about the quantity deposited in the device is not the same as the information provided by the analyzer 130, the record keeping authority reviews records, patient charts, etc., and contacts the controlled substance depositor and attempts to reconcile the discrepancy 560. Once the discrepancy is corrected, the substance is rendered unusable 570.

Advantages to the device as described by the present invention include eliminating the potential for a person to substitute any other clear liquid for a controlled substance, eliminating the need for a second medical professional to witness the disposal event, reducing the time required to dispose of controlled substances, expediting the review and reconciliation of the controlled substance transaction, and eliminating the possibility for a person to illegally acquire medications that have been disposed.

While the invention may be adapted to various modifications and alternative forms, specific embodiments have been shown by way of example and described herein. However, it should be understood that the invention is not intended to be limited to the particular forms disclosed. Rather, the invention is to cover all modifications, equivalents and alternatives falling within the spirit and scope of the invention as defined by the appended claims. Moreover, the different aspects of the disclosed apparatus and methods may be utilized in various combinations and/or independently and method steps may be performed in any order. Thus, the invention is not limited to only those combinations shown herein, but rather may include other combinations.

All references cited herein are incorporated by reference to the maximum extent allowable by law. To the extent a reference may not be fully incorporated herein, it is incorporated by reference for background purposes and indicative of the knowledge of one of ordinary skill in the art.

What is claimed is:

1. A method for the disposal of a controlled substance, comprising the steps of:
    collecting a controlled substance into a collector, said controlled substance being defined by a chemical composition concentration and amount, including storing said controlled substance to prevent access by unauthorized persons;
    receiving pre-analysis information about said controlled substance from a depositor of said controlled substance, wherein said pre-analysis information comprises a disclosed chemical composition, concentration and/or amount of said controlled substance;
    analyzing said controlled substance to determine the chemical composition, concentration and amount of said controlled substance;
    recording information about the chemical composition, concentration and amount of said controlled substance; and
    disposing of said controlled substance.

2. The method of claim 1, wherein the depositor of said controlled substance is an automated injection system.

3. A method for the disposal of a controlled substance, comprising the steps of:
    collecting a controlled substance into a collector, said controlled substance being defined by a chemical composition concentration and amount;
    receiving pre-analysis information about said controlled substance from a depositor of said controlled substance, wherein said pre-analysis information comprises a disclosed chemical composition concentration and/or amount of said controlled substance;
    analyzing said controlled substance to determine the chemical composition, concentration and amount of said controlled substance;
    recording information about the chemical composition, concentration and amount of said controlled substance;
    disposing of said controlled substance;
    reviewing the analysis of said controlled substance; and
    reconciling the recorded information about said controlled substance against information stored in an overseeing authority information system.

4. The method of claim 3, wherein the step of reviewing the analysis comprises verifying that the chemical composition, concentration and amount of said collected and analyzed controlled substance is identical to the pre-analysis information provided by the depositor of said controlled substance.

5. The method of claim 3, wherein the step of reconciling includes verifying said information stored in an overseeing authority information system with results discovered during said step of analyzing and with the pre-analysis information provided by the depositor of said controlled substance.

6. The method of claim 1, wherein the step of analyzing a controlled substance to determine said composition and concentration of said controlled substance is performed using Raman scattering techniques.

7. The method of claim 1, wherein the step of analyzing a controlled substance to determine said composition and concentration of said controlled substance is performed using surface plasmon resonance techniques.

8. The method of claim 5, wherein said information stored in said overseeing authority information system is a Medication Administration Report, anesthesia record, a pharmacy report of medications, information from an automated injection system, information from an automated drug dispensing system, or other types of data.

9. The method of claim 5, wherein the step of reconciling is automatic upon receiving information from said analysis, obtaining the pre-analysis information about said controlled substance from said depositor, and receiving information from said overseeing authority information system.

10. A system for disposing of controlled substances, comprising:
    a collector for receiving one or more amounts of controlled substances;
    an analyzer for determining the composition and concentration of a controlled substance received in said collector; and
    an information recorder for receiving pre-analysis information about the controlled substance from a depositor of the controlled substance, receiving post-analysis information about the analysis of the controlled substance from said analyzer, storing said pre-analysis and post-analysis information, and operable to transfer the pre-analysis and post-analysis information for subsequent reconciliation; and
    an overseeing authority information system operably connected to a network, wherein information is stored in said information recorder may be reconciled against information stored in said overseeing authority information system.

11. The system of claim 10, further comprising a disposer operable to dispose of said received controlled substance.

12. The system of claim 10, wherein said overseeing authority information system is configured for reconciling the information stored in said information recorder against information stored in said overseeing authority information system.

13. The system of claim 10, wherein said analyzer is configured for reconciling the information stored in said information recorder against information stored in said overseeing authority information system.

14. The system of claim 11, wherein said analyzer determines the composition or concentration based on Raman scattering techniques.

15. The system of claim 11, wherein said analyzer determines the composition or concentration based on surface plasmon resonance techniques.

16. The system of claim 11, wherein the pre-analysis information stored within said information recorder is received from an automated injection system.

17. A system for disposing of controlled substances, comprising:
- a collector for receiving one or more amounts of controlled substances adapted to prevent access by unauthorized persons;
- an analyzer for determining the composition and concentration of a controlled substance received in said collector; and
- an information recorder for receiving pre-analysis information about the controlled substance from a depositor of the controlled substance, receiving post-analysis information about the analysis of the controlled substance from said analyzer storing said pre-analysis and post-analysis information, and operable to transfer the pre-analysis and post-analysis information for subsequent reconciliation.

18. A method for collecting and analyzing a controlled substance, comprising:
- collecting a controlled substance deposit;
- analyzing said controlled substance deposit to determine chemical composition;
- determining the amount of said controlled substance deposit;
- receiving information from a depositor of said controlled substance indicating the chemical composition and amount of said controlled substance deposit;
- comparing said determined chemical composition and amount with said depositor information;
- recording said determined chemical composition and amount; and
- reconciling said recording and depositor information with information stored in an overseeing authority information system.

19. The method of claim 18, including analyzing said controlled substance deposit to determine concentration.

20. The method of claim 18, including recording said depositor information and the results of said comparing step.

21. The method of claim 18, including disposing of said controlled substance.

* * * * *